US010632314B1

(12) United States Patent
Perryman et al.

(10) Patent No.: US 10,632,314 B1
(45) Date of Patent: Apr. 28, 2020

(54) USER INTERFACE FOR A PATIENT USER TO ADJUST SETTINGS ON AN IMPLANTABLE DEVICE

(71) Applicant: Stimwave Technologies Incorporated, Fort Lauderdale, FL (US)

(72) Inventors: Laura Tyler Perryman, Fort Lauderdale, FL (US); Chad David Andresen, Miami Beach, FL (US); D. Alan Corbett, Fort Lauderdale, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 309 days.

(21) Appl. No.: 15/620,165

(22) Filed: Jun. 12, 2017

Related U.S. Application Data

(60) Provisional application No. 62/348,188, filed on Jun. 10, 2016.

(51) Int. Cl.
*A61N 1/00* (2006.01)
*A61N 1/372* (2006.01)
(Continued)

(52) U.S. Cl.
CPC ..... *A61N 1/37247* (2013.01); *A61N 1/36071* (2013.01); *A61N 1/36132* (2013.01);
(Continued)

(58) Field of Classification Search
None
See application file for complete search history.

(56) References Cited

U.S. PATENT DOCUMENTS

| 8,849,412 B2 * | 9/2014 | Perryman | A61N 1/37229 607/60 |
| 9,731,140 B1 * | 8/2017 | Perryman | A61N 1/37264 |
| 2016/0008602 A1 | 1/2016 | Perryman et al. | |

FOREIGN PATENT DOCUMENTS

| WO | WO 2012/103519 | 8/2012 |
| WO | WO 2012/138782 | 10/2012 |

(Continued)

*Primary Examiner* — Brian T Gedeon
(74) *Attorney, Agent, or Firm* — Fish & Richardson P.C.

(57) ABSTRACT

A computer-assisted method that includes: establishing a communication link between a programming device and a controller device, the controller device wirelessly and non-inductively powering and controlling a passive implantable stimulator device; presenting configuration options to the patient user of the passive implantable stimulator device, the configuration options comprising stimulation waveform parameters for driving the passive implantable stimulator; receiving a specification of the configuration options in response to the presented configuration options; receiving user feedback when the user specified configuration options are transferred to the controller device which, in turn, drives the implantable stimulator device according to the specified configuration options; building, at the programming device, a profile that correlates the user specified configuration options with the corresponding quantitative index of pain; and recommending at least one configuration option based on the profile built from historic data when the configuration options are subsequently presented to the patient user for later treatment.

18 Claims, 9 Drawing Sheets

(51) Int. Cl.
*A61N 1/378* (2006.01)
*A61N 1/36* (2006.01)
(52) U.S. Cl.
CPC ......... *A61N 1/3727* (2013.01); *A61N 1/3787* (2013.01); *A61N 1/37229* (2013.01)

(56) References Cited

FOREIGN PATENT DOCUMENTS

| WO | WO 2013/019757 | 2/2013 |
| WO | WO 2013/025632 | 2/2013 |
| WO | WO 2013/040549 | 3/2013 |

\* cited by examiner

USER INTERFACE FOR A PATIENT USER TO ADJUST SETTINGS ON AN IMPLANTABLE DEVICE

CROSS-REFERENCE TO RELATED APPLICATION

This application claims the benefit of U.S. Provisional Application No. 62/348,188, filed Jun. 10, 2016, and titled "User Interface for a Patient User to Adjust Settings on an Impantable Device," which is incorporated by reference.

TECHNICAL FIELD

This application relates generally to implantable stimulators.

BACKGROUND

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing. Typically, such devices utilize a subcutaneous battery operated implantable pulse generator (IPG) to provide power or other charge storage mechanisms.

SUMMARY

In one aspect, some implementations provide a computer-assisted method for a patient user to control settings for a stimulator system, the method including: establishing a communication link between a programming device and a controller device, the controller device configured to wirelessly and non-inductively provide power to and assert control over a passive implantable stimulator device implanted inside the patient user; presenting, on the programming device, configuration options to the patient user of the passive implantable stimulator device, the configuration options comprising stimulation waveform parameters for driving the passive implantable stimulator; receiving, from the patient user on the programming device, a specification of the configuration options in response to the presented configuration options; receiving user feedback, from the patient user on the programming device, when the user specified configuration options are transferred to the controller device which, in turn, drives the implantable stimulator device according to the specified configuration options, the user feedback comprising a quantitative index of pain resulting from driving the implantable stimulator device according to the user specified configuration options; building, at the programming device, a profile for the patient user based on the user specified configuration options and the feedback from the patient user, the profile correlates the user specified configuration options with the corresponding quantitative index of pain; and recommending, at the programming device, at least one configuration option based on the profile built from historic data when the configuration options are subsequently presented to the patient user for a later treatment.

Implementations may include one or more of the following features. Establishing a communicating link between a programming device and a controller device may include: establishing a wireless communication link between the programming device and the controller device such that data encoding configuration options are transmitted over the wireless communication link from the programming device to the controller device. Establishing a communicating link between a programming device and a controller device may include: establishing a wired communication link between the programming device and the controller device such that data encoding configuration options are transmitted over the wired communication link from the programming device to the controller device. Implementations may further include: presenting, on the programming device, a graphic user interface over which configuration options are presented to the patient user of the implanted passive implantable stimulator device, the specification of the configuration options are received from the patient user in response to the presented configuration options, and feedback are received from the patient user the implanted stimulator device operating according to the specified configuration option.

In some implementations, building a profile for the patient user based on the user specified configuration options and the feedback from the patient user may include: assembling user specified configuration options that include all selected permutations of the stimulation waveform parameters from various treatments; and determining a correlation between a particular permutation of the stimulation parameters with a quantitative index of pain as reported by the patient user when the correlation becomes statistically significant. Determining a correlation between a particular permutation of the stimulation parameters with a quantitative index of pain as reported by the patient user further may include: establishing the correlation based on a time window when a treatment is rendered. Determining a correlation between a particular permutation of the stimulation parameters with a quantitative index of pain as reported by the patient user may further include: determining the correlation by merging permutations of the stimulation parameters when the permutations of the stimulation parameters are statistically similar in inducing a particular quantitative index of pain.

In some implementations, receiving user feedback may include receiving information of a quantitative index of pain expressed as improvement over a baseline of pain, the improvement resulting from driving the implanted stimulator device according to the user specified configuration options. Recommending at least one configuration option may include recommending a particular permutation of stimulation waveform parameters to the patient user for the later treatment. The method may further include: selecting the particular permutation of stimulation parameters as more likely than other permutations to render a desired improvement over a baseline of pain for the later treatment.

In another aspect, some implementations provide a programming device, coupled to a controller device to control settings on an implanted stimulator device, the programming device including: a processor; and a user interface in communication with the processor, wherein the processor is configured to perform the operations of: establishing a communication link between the programming device and the controller device, the controller device configured to wirelessly and non-inductively provide power to and assert control over a passive implantable stimulator device implanted inside the patient user; presenting, on the user interface, configuration options to the patient user of the passive implantable stimulator device, the configuration options comprising stimulation waveform parameters for driving the passive implantable stimulator; receiving, from the patient user on the user interface, a specification of the configuration options in response to the presented configuration options; receiving user feedback, from the patient user on the user interface, when the user specified configuration options are transferred to the controller device which, in turn, drives the implantable stimulator device according to the specified configuration options, the user feedback comprising a quantitative index of pain resulting from driving the implantable stimulator device according to the user specified configuration options; building a profile for the patient user based on the user specified configuration options and the feedback from the patient user, the profile correlates the user specified configuration options with the corresponding quantitative index of pain; and recommending, on the user interface, at least one configuration option based on the profile built from historic data when the configuration options are subsequently presented to the patient user for a later treatment.

Implementations may include one or more of the following features. Establishing a communicating link between the programming device and the controller device comprises: establishing a wireless communication link between the programming device and the controller device such that data encoding configuration options are transmitted over the wireless communication link from the programming device to the controller device. Establishing a communicating link between the programming device and the controller device may include: establishing a wired communication link between the programming device and the controller device such that data encoding configuration options are transmitted over the wired communication link from the programming device to the controller device.

The processor may be further configured to perform the operation of: presenting, on the user interface, a touch screen interface tool over which configuration options are presented to the patient user of the implanted passive implantable stimulator device, the specification of the configuration options are received from the patient user in response to the presented configuration options, and feedback are received from the patient user the implanted stimulator device operating according to the specified configuration option.

Building a profile for the patient user based on the user specified configuration options and the feedback from the patient user may include: assembling user specified configuration options that include all selected permutations of the stimulation waveform parameters from various treatments; and determining a correlation between a particular permutation of the stimulation parameters with a quantitative index of pain as reported by the patient user when the correlation becomes statistically significant.

Determining a correlation between a particular permutation of the stimulation parameters with a quantitative index of pain as reported by the patient user may further include: establishing the correlation based on a time window when a treatment is rendered. Determining a correlation between a particular permutation of the stimulation parameters with a quantitative index of pain as reported by the patient user may further include: determining the correlation by merging permutations of the stimulation parameters when the permutations of the stimulation parameters are statistically similar in inducing a particular quantitative index of pain.

Receiving user feedback may include receiving information of a quantitative index of pain expressed as improvement over a baseline of pain, the improvement resulting from driving the implanted stimulator device according to the user specified configuration options. Recommending at least one configuration option may include recommending a particular permutation of stimulation waveform parameters to the patient user for the later treatment.

The processor may be further configured to perform the operation of: selecting the particular permutation of stimulation parameters as more likely than other permutations to render a desired improvement over a baseline of pain for the later treatment.

Various implementations may be inherently low in cost compared to existing implantable neural modulation systems, and this may lead to wider adoption of neural modulation therapy for patients in need as well as reduction in overall cost to the healthcare system.

The details of one or more implementations are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
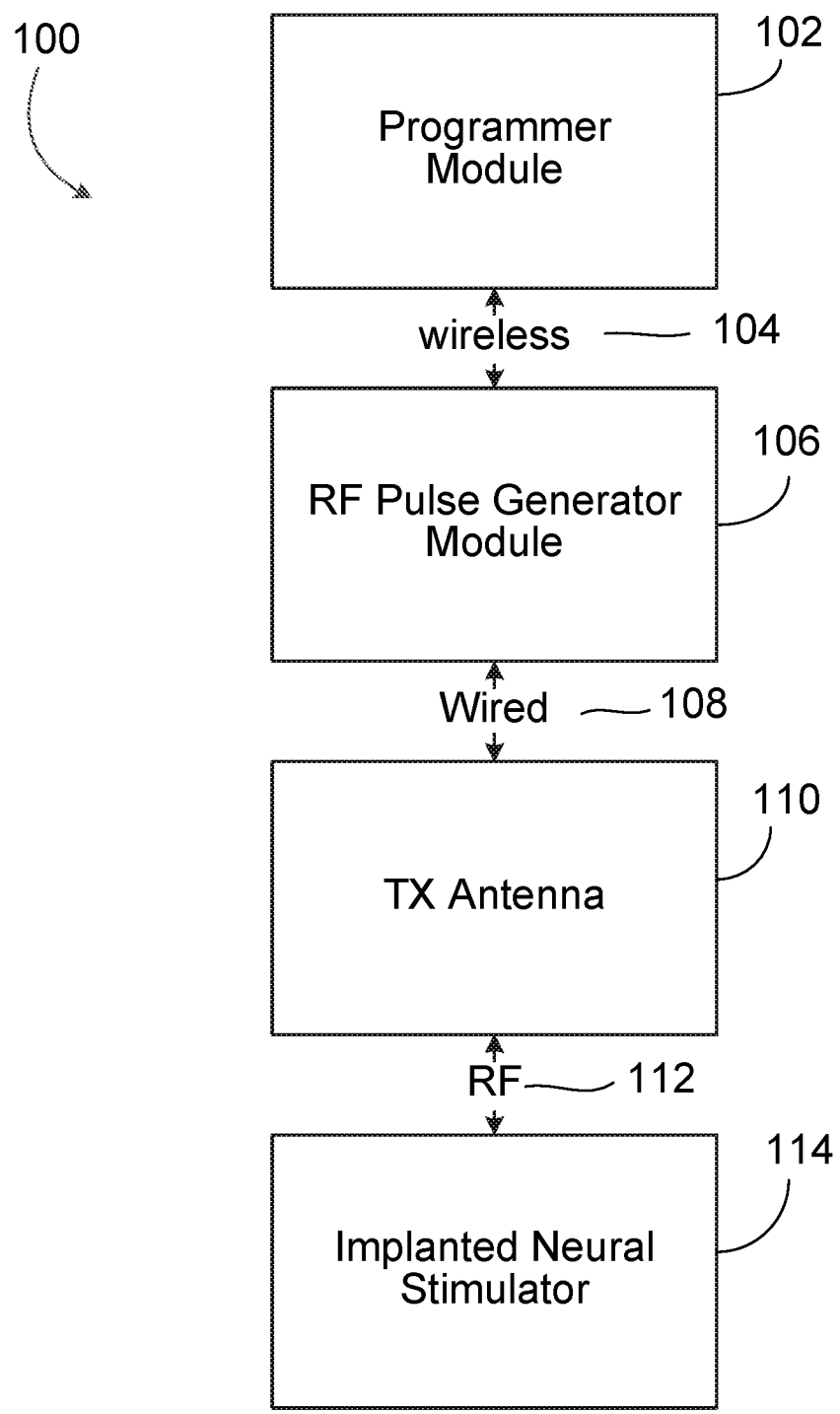
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

Some implementations may include a user interface for a patient user to access therapeutic settings so that a user can individualize parameter settings for each therapeutic session without the need to call up a healthcare professional—for example, a nurse, or a physician. The user interface can be implemented on a portable computing device as, for example, an application (App) program. The portable computing device may include a tablet device such as an iPad, a Nexus tablet, etc. The portable computing device may communicate with a microwave field stimulator (MFS) that couples to a passive implantable neural stimulator device by non-inductive electric radiative coupling such that the passive implantable neural stimulator device is wirelessly powered without an on-board battery. The user interface allows a user to adjust therapeutic settings on the passive implantable neural stimulator device on an individualized basis without interventions from a clinician. The user adjustments may be limited in range and applicable parameters to ensure safety settings are not breached and regulatory limits are not exceeded. The user interface may also include a user feedback to record the user's response to particular settings. A user profile can be built up based on user's past choices and user feedback so that the user interface may present to the user a judiciously chosen parameter setting based on earlier choices and feedback. The presented parameters may represent the parameter setting that is believed to be the most appropriate for a particular patient for treating a given target. The intelligently-chosen parameter setting may speed up the configuration of user parameter settings, thereby enhancing user experience.

Further descriptions of exemplary wireless systems for providing neural stimulation to a patient can be found in commonly-assigned, co-pending published PCT and US applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011, and PCT/US2012/55746, filed Sep. 15, 2011, US2016/0008602 filed Jul. 19, 2015, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electromagnetic radiative coupling, the TX antenna 110 can provide an input signal to the implanted wireless stimulator device 114. Within the implanted wireless stimulator device 114 are components for demodulating the RF transmission signal, and electrodes to deliver the stimulation to surrounding neuronal tissue. The input signal contains electrical energy to power the creation of a stimulation waveform so that the stimulation waveform can be synthesized and applied at the electrodes. The power level of the electrical energy in the input signal ultimately determines an applied amplitude (for example, power, current, or voltage) of the one or more electrical pulses created using the electrical energy contained in the input signal. In some implementations, the input signal can contain information based on which stimulus waveforms to be synthesized and applied at the electrodes of the implanted wireless stimulator device 114. In one example, the input signal can encode, for example, delay information, or repetition rate information and waveform characteristics as well address information point to a portion of a read-only memory (ROM) on the implantable stimulator device. In this example, the delay information may indicate the amount of latency that the stimulation waveform may be synthesized. The address information refers to the storage location on the ROM to retrieve a pulse-density modulated representation of the desired stimulation waveform.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 can capture the energy radiated by the TX antenna 110 and use this energy to synthesize a stimulation waveform.

The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the tissue characteristics the electrode pads see. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
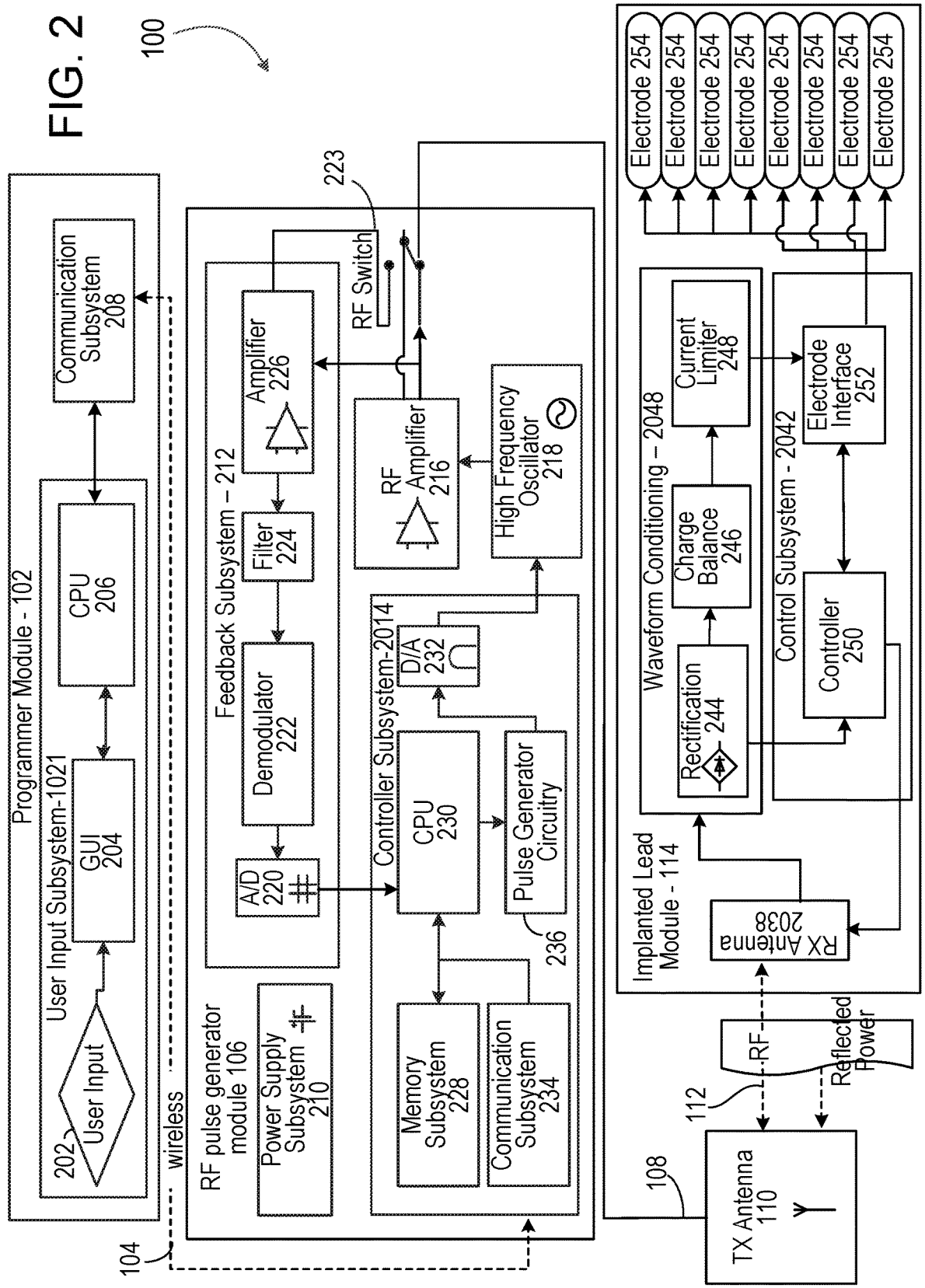
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send information to the RF pulse generator module 106 such that stimulation parameters (e.g., pulse amplitude, pulse frequency, and pulse width) can be controlled. Example ranges of stimulation parameters are shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

| Stimulation Parameter Table 1 | |
|---|---|
| Pulse Amplitude: | 0 to 20 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and/or an associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include electrical power and configuration data based on which to recover pulse attributes such as stimulus waveform, amplitude, pulse width, and repetition frequency. The configuration data may also include polarity setting information designating the polarity setting for each electrode. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and single-bit oversampled (EA) digital/analog (D/A) converters or single-bit controlled full-bridge drivers 232. In other implementations, a Nyquist rate multi-bit D/A converters can also be used for stimulus generation.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a signal that would enable the synthesis of the desired stimulation waveform on the implantable stimulator device 114. The signal can be modulated by a high frequency carrier signal generated by an oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238. In the case where a single-bit pulse density modulated waveform is used for stimulus generation, a local oscillator in the range of 1 MHz is used to read-in the bitstream from a ROM device.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114, which telemetry signal includes instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) using one of the several modulation methods including On-Off Keying (OOK), Pulse-Amplitude Modulation (PAM), Phase-shift Keying (PSK) and Frequency-Shift Keying (FSK) and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment arrangements such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path. An A/D (not shown) converter can be used to transform stored data to a serialized pattern that can be transmitted on the pulse-modulated telemetry signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes, or impedance of the tissue. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform generation circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning and generation circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced with zero net charge output). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse (i.e., the input signal) directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

Figure 3A:
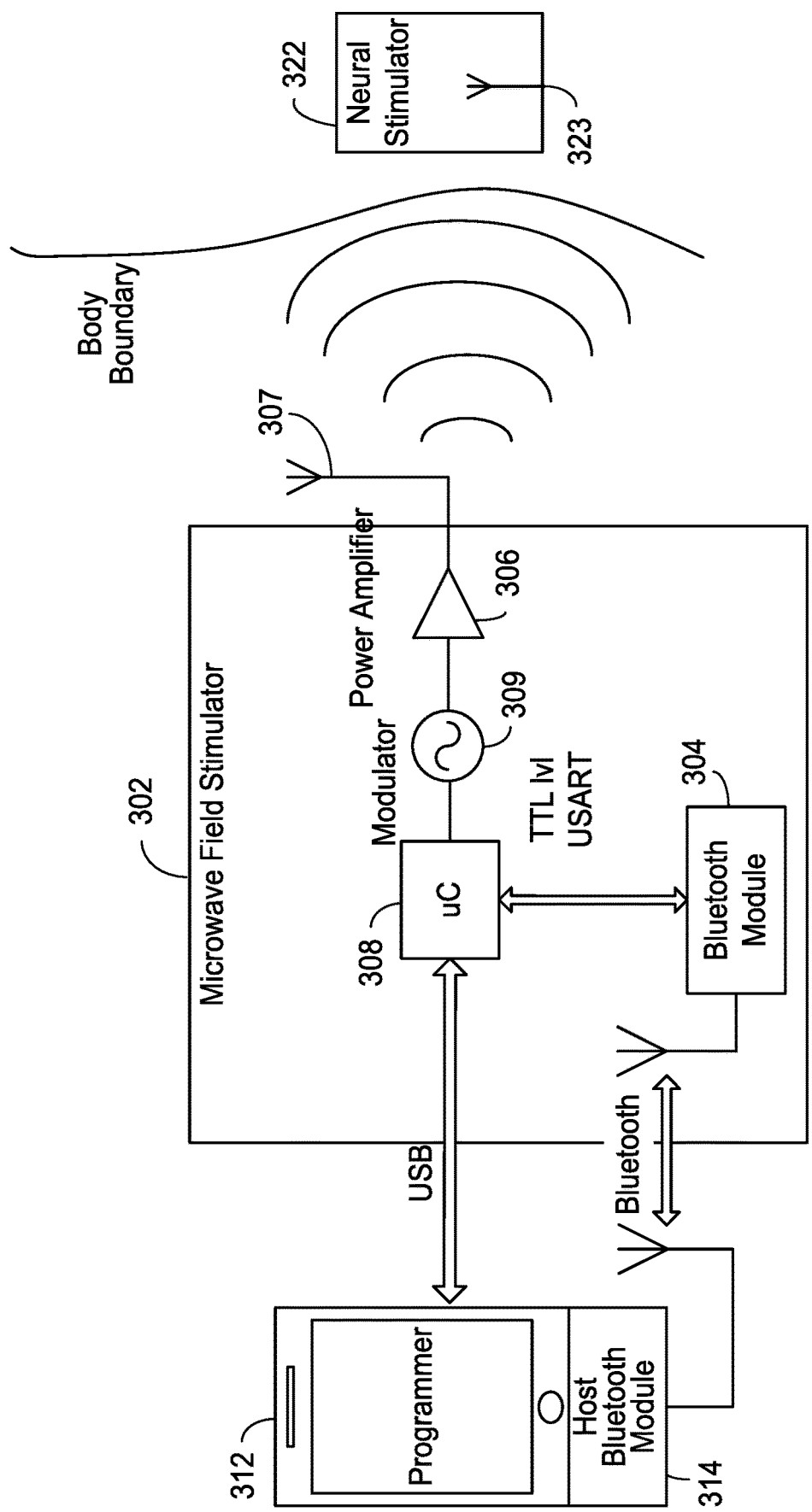
FIG. 3A is a diagram of an example microwave field stimulator (MFS) operating along with an implantable stimulation device.

FIG. 3A is a diagram of an example implementation of a microwave field stimulator (MFS) 302 as part of a stimulation system utilizing an implantable, passive device 322. In this example, the MFS 302 is external to a patient's body and may be placed within in close proximity, for example, within 3 feet, to an implantable, passive 322. The RF pulse generator module 106 may be one example implementation of MFS 302. MFS 302 may be generally known as a controller module. The implanted lead module 114 may be one example of an implantable, passive simulation device 322. The implantable, passive simulation device 322 is a passive device. The implantable, passive stimulation device does not have its own independent power source, rather it receives power for its operation from transmission signals emitted from a TX antenna powered by the MFS 302, as discussed above.

In certain embodiments, the MFS 302 may communicate with a programmer 312. The programmer 312 may be a mobile computing device, such as, for example, a laptop, a smart phone, a tablet, etc. The communication may be wired, using for example, a USB or firewire cable. The communication may also be wireless, utilizing for example, a bluetooth protocol implemented by a transmitting blue tooth module 304 which communicates with the host bluetooth module 314 within the programmer 312. A user, such as a patient, company representative, or a doctor may use the programmer 312 to send stimulation information to the MFS 312, which stores the stimulation information. The stimulation information may include, for example, the polarity of the electrodes in the implantable, passive stimulation device 322 and/or the parameters defining the stimulation waveform.

The MFS 302 may additionally communicate with implantable, passive stimulation device 322 by transmitting a transmission signal through a TX antenna 307 coupled to an amplifier 306. The transmission signal may propagate through skin and underlying tissues to arrive at the RX antenna 323 of the implantable, passive stimulation device 322. As discussed in further detail below, this transmission signal may encode polarity assignments for the electrodes in the stimulation device 322 and include the stimulation waveform. In some implementations, the implantable, passive stimulation device 322 may transmit a telemetry feedback signal back to MFS 302.

The MFS 302 may include a microcontroller 308 configured to manage the communication with a programmer 312 and generate an output signal based on the stimulation information sent from the programmer. The output signal may be used by the modulator 309 to modulate a RF carrier signal to generate the transmission signal. The frequency of the carrier signal may be in the microwave range, for example, from about 300 MHz to about 8 GHz. This frequency may be known as the stimulus carrier frequency. The modulated RF carrier signal may be amplified by an amplifier 306 to provide the transmission signal for transmission to the implantable, passive stimulation device 322 through a TX antenna 307.

Figure 3B:
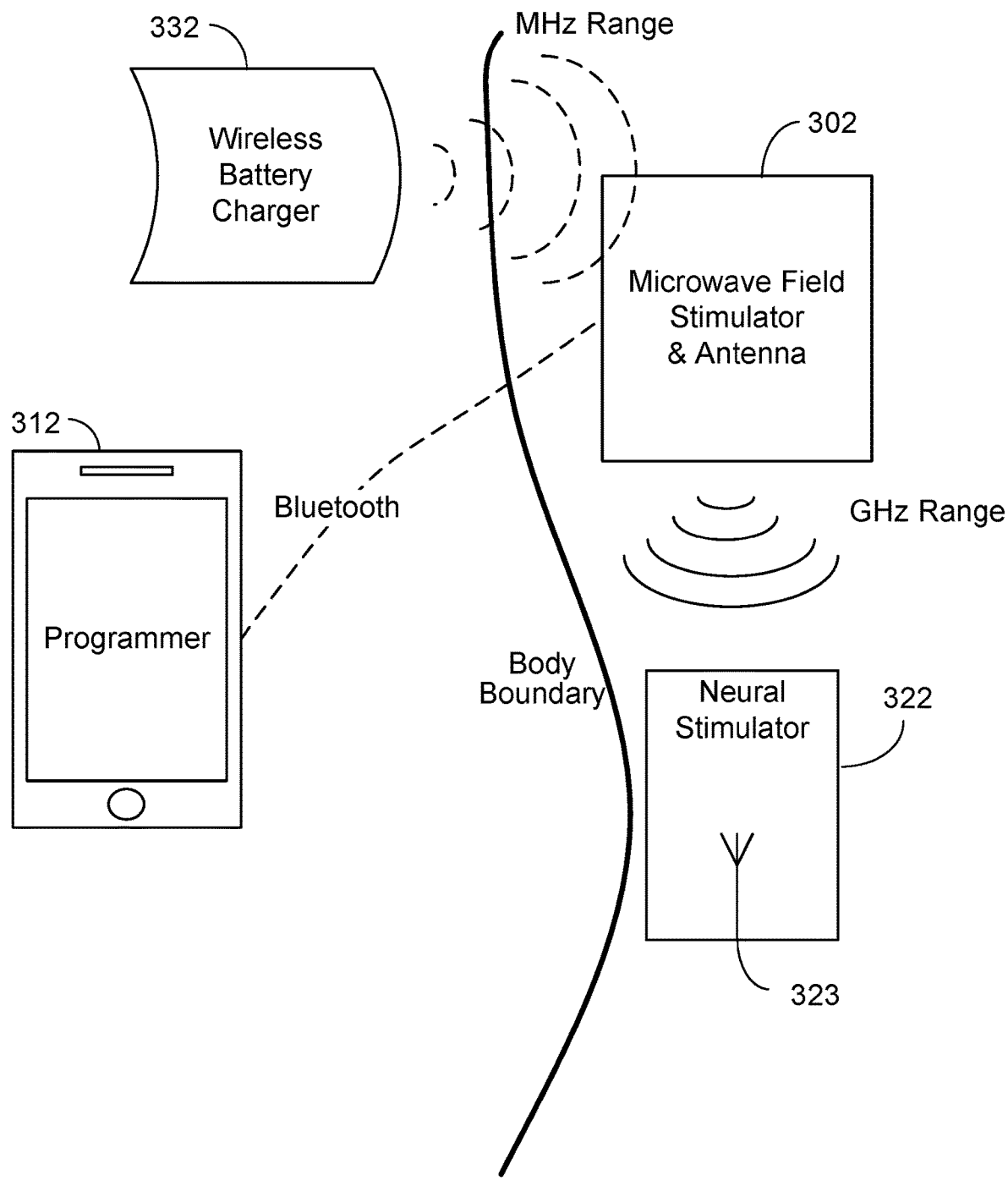
FIG. 3B is a diagram of another example microwave field stimulator (MFS) operating along with an implantable stimulation device.

FIG. 3B is a diagram of another example of an implementation of a microwave field stimulator 302 as part of a stimulation system utilizing an implantable, passive neural stimulator 322. In this example, the MFS 302 may be embedded in the body of the patient, for example, subcutaneously. The embedded MFS 302 may receive power from a detached, remote wireless battery charger 332.

The power from the wireless battery charger 332 to the embedded MFS 302 may be transmitted at a frequency in the MHz or GHz range and via inductive coupling. The MFS 302 may be embedded subcutaneously at a very shallow depth (e.g., less than 1 cm), inductive coupling to transfer energy from wireless battery charger 332 to the embedded MFS 302 may be feasible and efficient.

In some embodiments, the MFS 302 may be adapted for placement at the epidural layer of a spinal column, near or on the dura of the spinal column, in tissue in close proximity to the spinal column, in tissue located near a dorsal horn, in dorsal root ganglia, in one or more of the dorsal roots, in dorsal column fibers, or in peripheral nerve bundles leaving the dorsal column of the spine.

In this embodiment, the MFS 302 may transmit power and parameter signals to a passive TX antenna also embedded subcutaneously, which may be coupled to the RX antenna within the implanted, passive stimulation device. The power required in this embodiment is substantially lower since the TX antenna and the RX antenna are already in body tissue and there is no requirement to transmit the signal through the skin.

Figure 4:
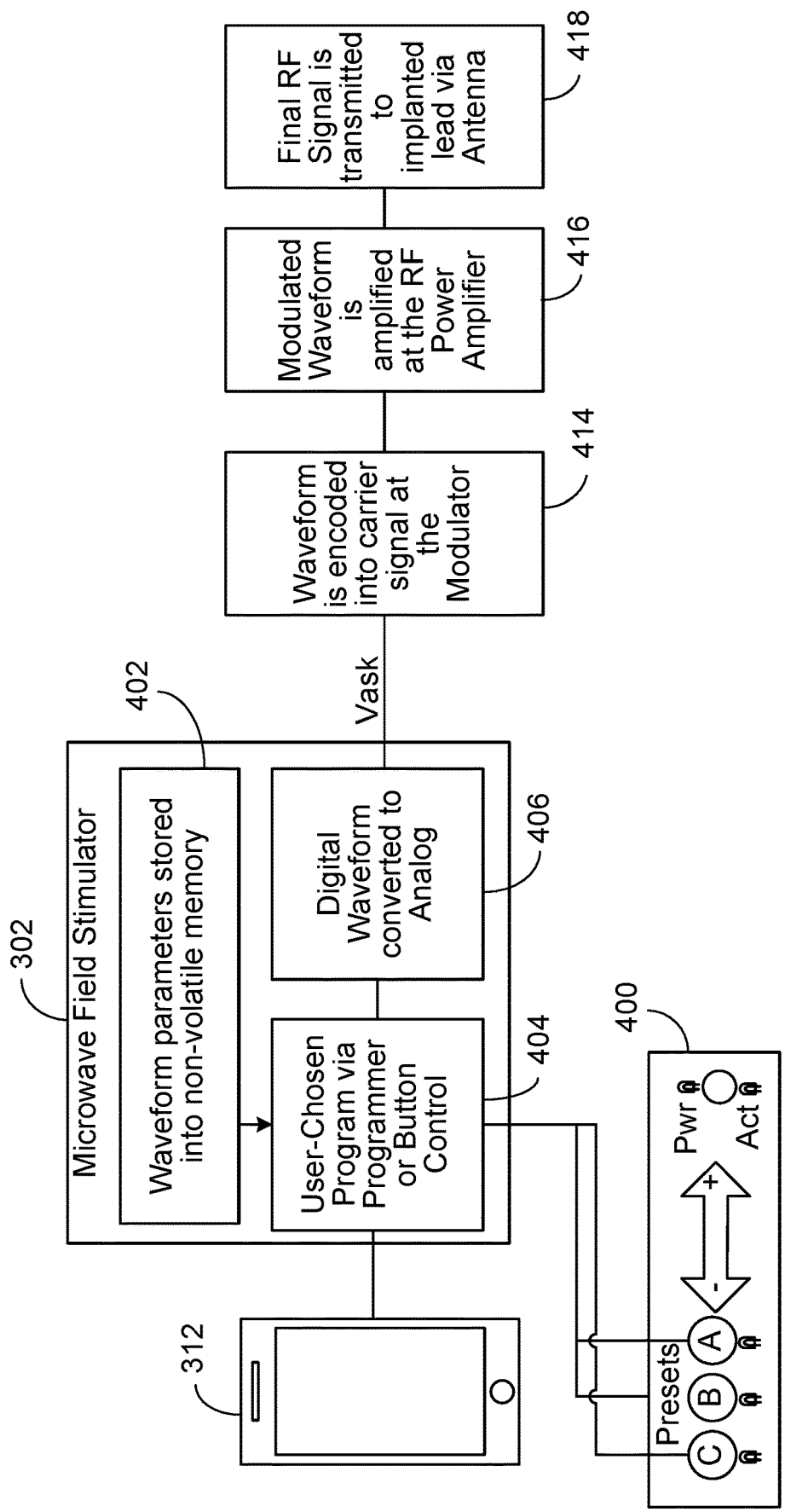
FIG. 4 is a block diagram illustrating an example in which a user programs the stimulation waveform to be embedded in the signal sequence for transmission to the implanted lead module.

FIG. 4 is a block diagram illustrating an example in which a user programs the stimulation waveform to be embedded in the signal sequence for transmission to the implantable, passive stimulation device 322. The programmer 312 may be a mobile computing device. The programmer 312 may communicate with the MFS 302 via, for example, bluetooth or USB. The user may authenticate him or herself to the MFS before he can access data on the MFS 302 or modify existing settings on the MFS 302. The communication may also be encrypted.

A user may modify a setting of the MFS 302 by, for example, choosing a preset program or using a button control (404). A user of the programmer 312 may be presented with a user interface (UI) 400. The UI 400 may be a visual programming interface to provide easy access to programming capabilities. The UI 400 may provide a collection of preset programs that the user may choose to apply to his treatment. The preset programs A, B, and C may be provided by the manufacturer as treatment protocols in compliance with any regulatory provisions. The preset programs may prescribed by an attending physician as the treatment plans most likely to be efficacious for the user/patient. The UI 308 may also provide a button for the user/patient to adjust a power level of the stimuli to be or being applied.

In some implementations, the UI 400 may provide debouncing in response to user inputs. After receiving user selections as made on the UI 308, waveform parameters stored in a non-volatile memory may be activated (402) so that the micro-controller 308 may synthesize an output signal based on the waveform parameters. The synthesized output signal may be converted into an analog signal (406). As discussed above, the analog signal may modulate a carrier frequency to provide a modulated signal (416), the modulated signal may be subsequently amplified by amplifier 306 (416), and the amplified signal may be transmitted from the MFS 302 to the implantable, passive stimulation device 322 (418).

Figure 5B:
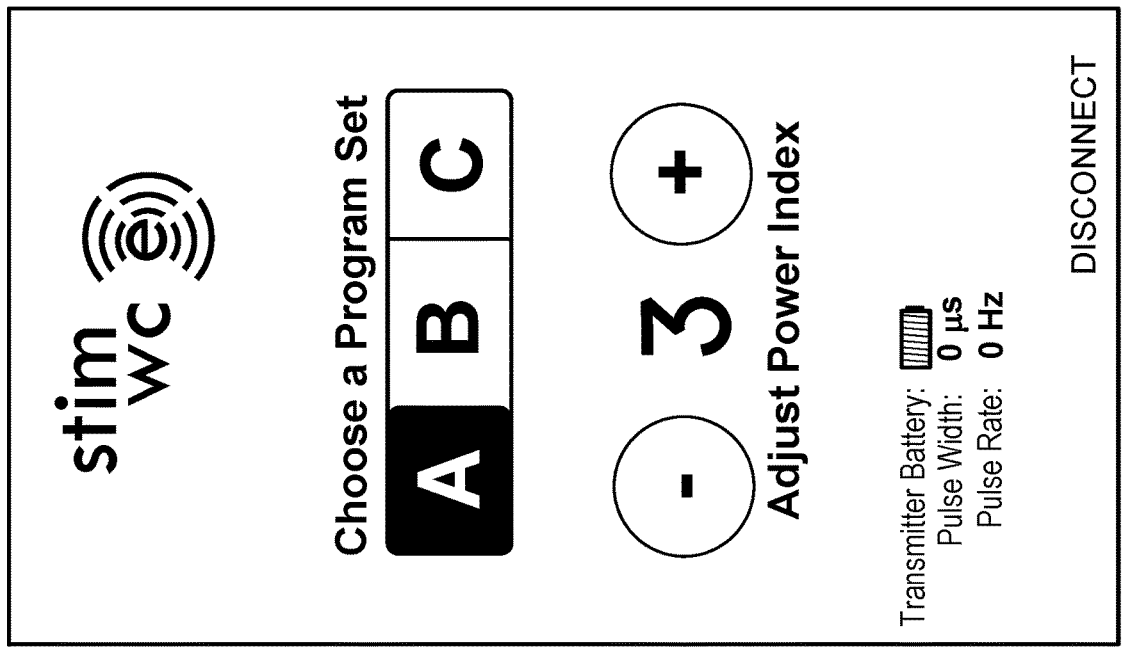
FIG. 5A-5H show examples of user interfaces for a patient user to access therapeutic settings that can be applied to an implantable neural stimulator device implanted in the patient.
Figure 5A:
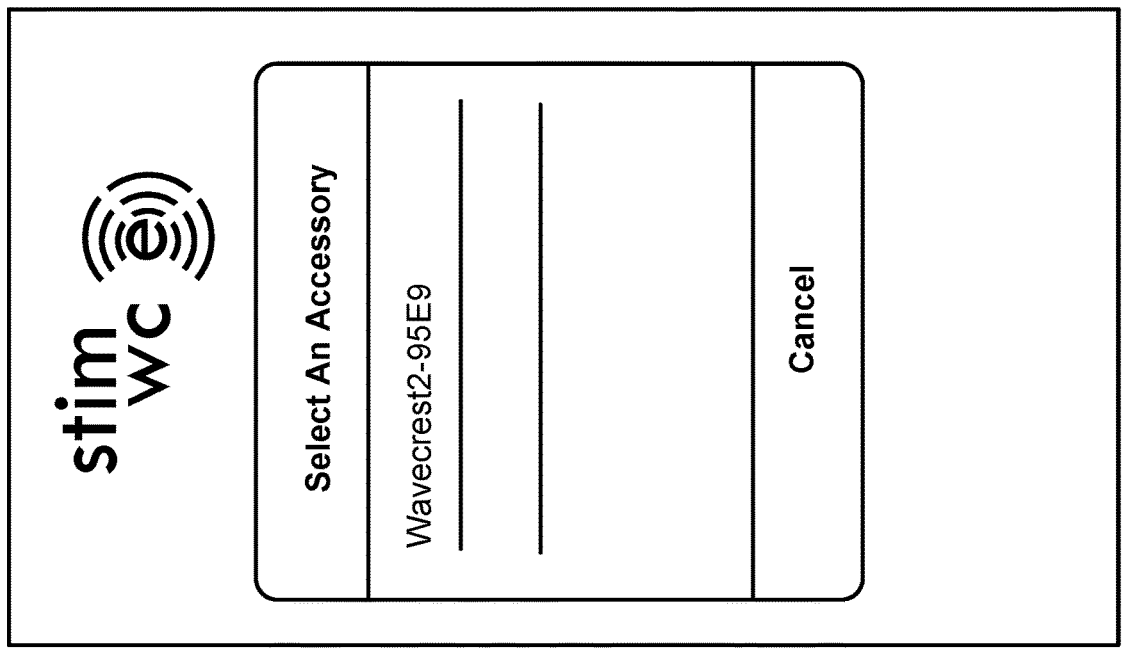

FIGS. 5A-5H show examples of user interfaces for a patient user to access therapeutic settings. FIG. 5A illustrates the wavecrest 2.3 patient app for iPhone/iPod that connects a MFS device wirelessly allowing for private, discreet adjustment of stimulation parameters on the neural stimulator. The user interface is conveniently located on a tablet device. The patient's transmitter need not be visible for wavecrest 2.3 operation. Once a user has chosen the app icon, the app will launch to reveal adjustment options, as detailed in FIGS. 5B-5G below.

In some implementations, the patient user can adjust stimulation power index to increase or decrease the power setting on the implantable neural stimulator device, as illustrated in FIG. 5B. In particular, panel 501 presents three programs—namely, A, B, and C—to select. Control button 502A and control button 502B respectively allow a patient user to decrease and increase power index which is representative on a logarithmic scale of dB. In this illustration, the decrement or increment is 3. Area 503 shows an icon for transmitter battery. This represents the amount of battery energy on the MFS device. Area 504 shows pulse width in units of µs.

Figure 5D:
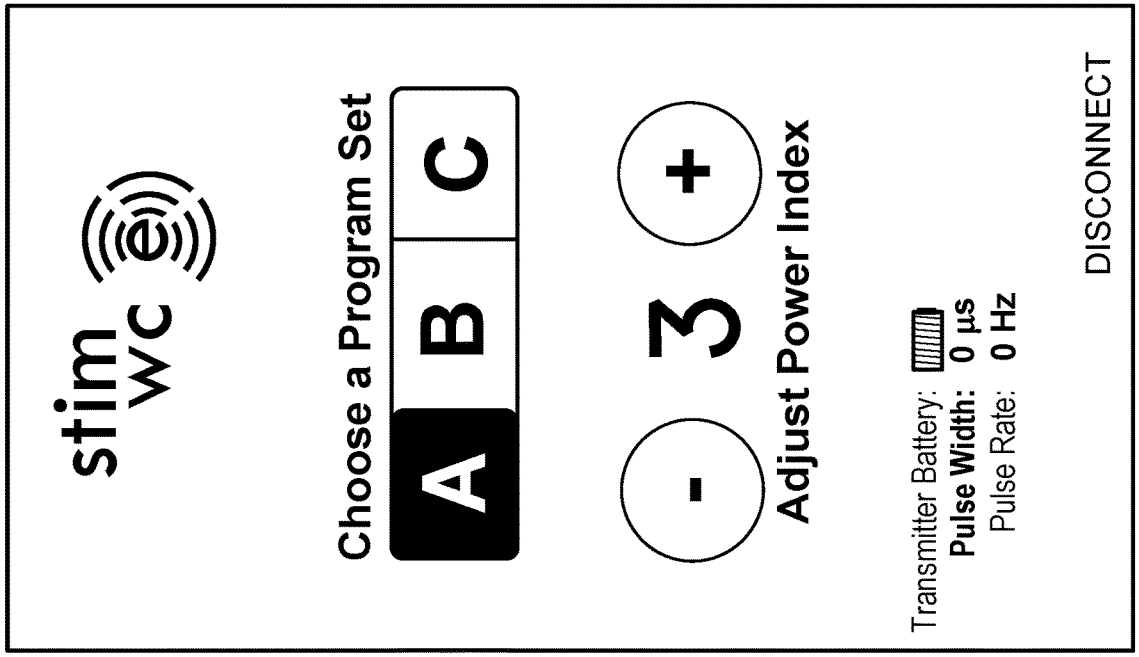
Figure 5C:
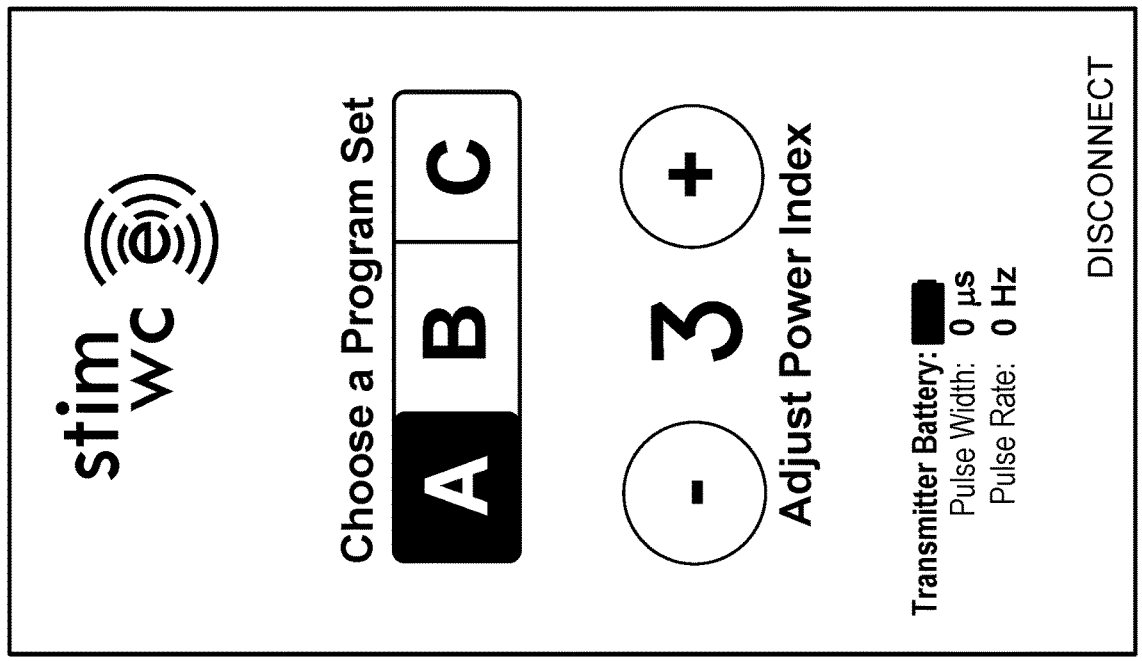
Figure 5F:
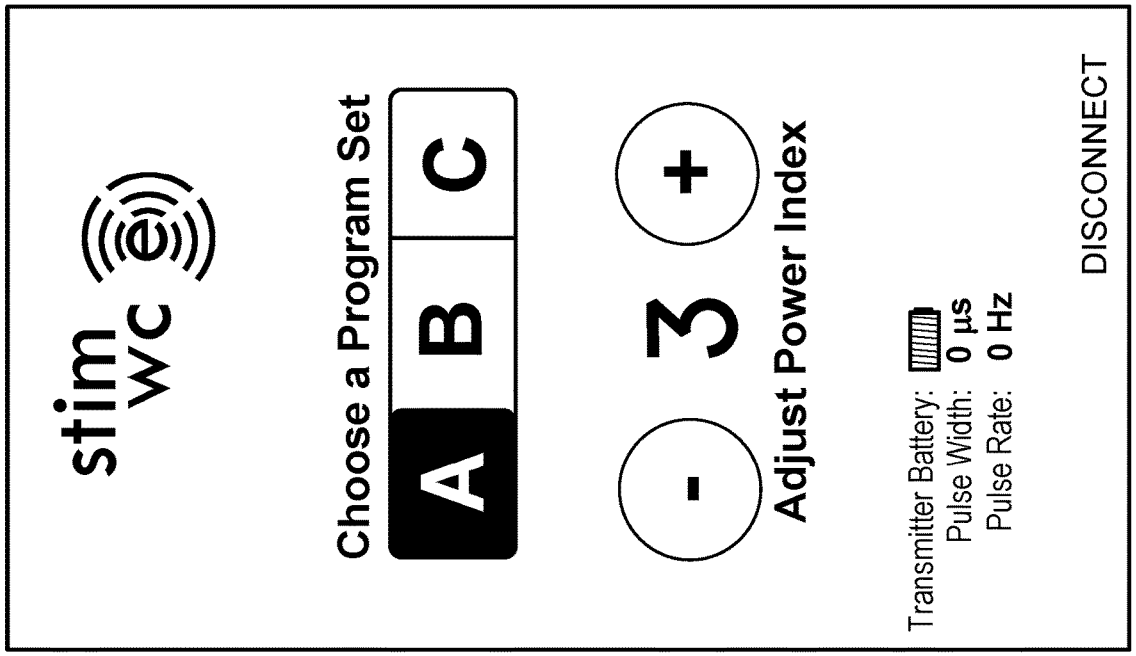
Figure 5E:
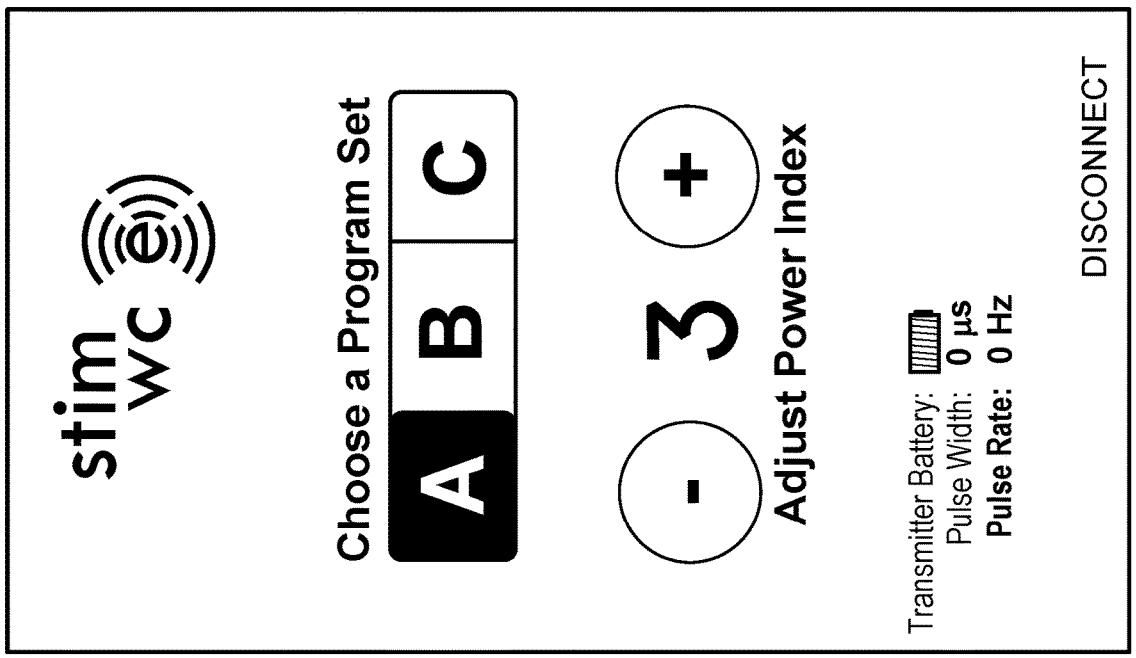

As illustrated in FIG. 5C, touch area 503 may including bar area 503A—showing currently remaining power of the MFS device, and icon 503B—showing touch screen bar, the tapping of which would reveal currently remaining power in bar area 503A. As illustrated in FIG. 5D, touch area 504B may be tapped to adjust pulse width as indicated in area 504A. FIG. 5E further illustrates touch area 505B that can be tapped to adjust pulse rate—shown in area 505A.

Figure 5H:
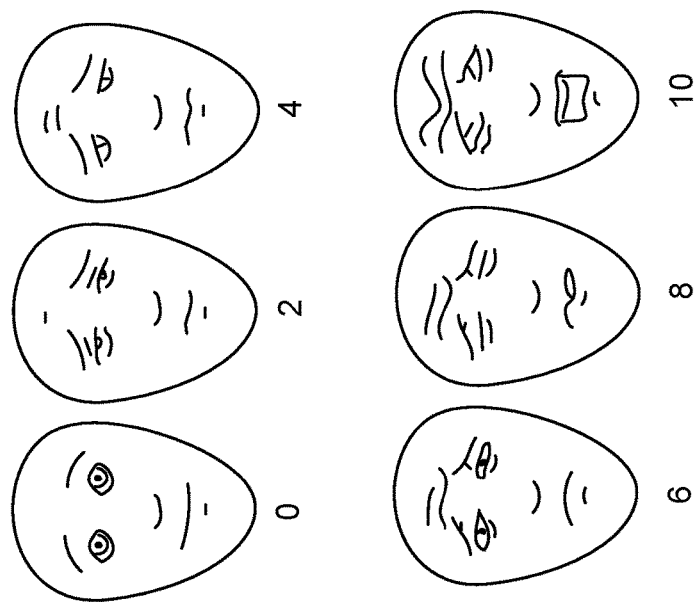
Figure 5G:
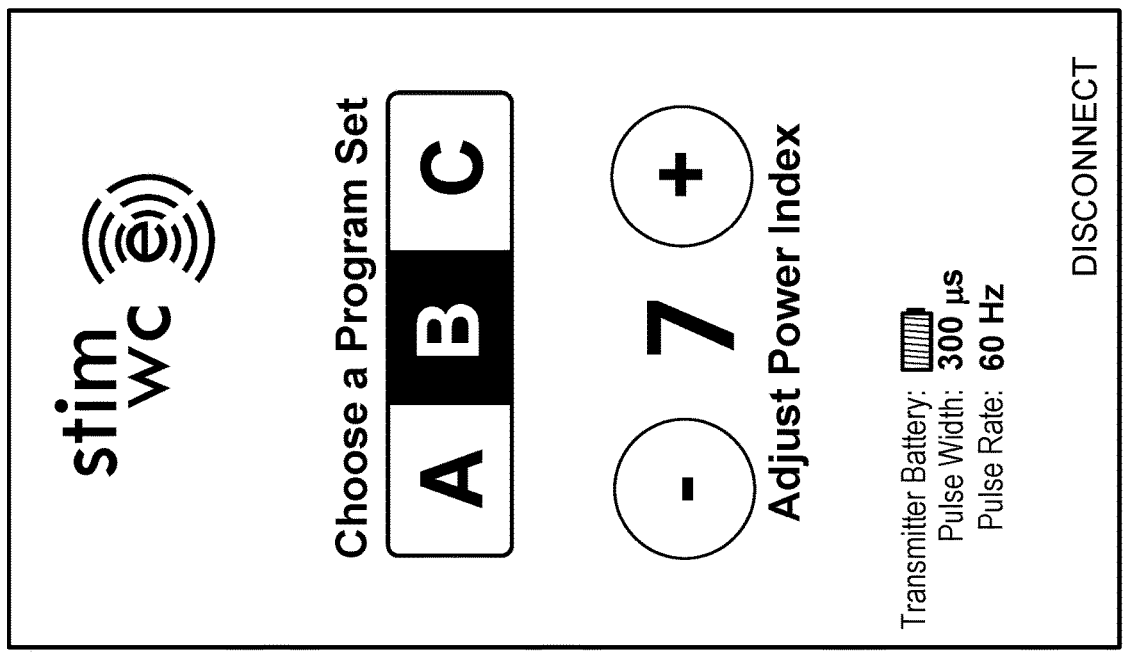

A patient can choose from three program sets (configured by the clinician in advance) using the Wavecrest™ clinician app. A program set may contain parameter settings for pulse rate, width, amperage and pulse pattern as well as ASIC settings. In the illustrated example of FIG. 5F, for instance, a patient may find greater relief in the mornings with program set A. The patient may find greater relief in the evenings on program set B, as shown in FIG. 5G. The determination of patient relief may be collected from user feedback. A convenient interface may collect user feedback by presenting a group of icons—as shown in FIG. 5H—each representing a numerical pain level by a corresponding facial expression showing more smiles for less pain and more frowns for more pain. As indicated, the pain level may be indexed from 0 to 10, with 0 indicating little or no pain, and 10 meaning the highest level of pain.

A number of implementations have been described. Nevertheless, it will be understood that various modifications may be made. Accordingly, other implementations are within the scope of the following claims.

What is claimed is:

1. A computer-assisted method for a patient user to control settings on an implanted stimulator device, the method comprising:

establishing a communication link between a programming device and a controller device, the controller device configured to wirelessly and non-inductively provide power to and assert control over a passive implantable stimulator device implanted inside the patient user;

presenting, on the programming device, configuration options to the patient user of the passive implantable stimulator device, the configuration options comprising stimulation waveform parameters for driving the passive implantable stimulator;

receiving, from the patient user and on the programming device, user specified configuration options in response to the presented configuration options;

receiving a user feedback, from the patient user and on the programming device, when the user specified configuration options are transferred to the controller device which, in turn, drives the implantable stimulator device according to the user specified configuration options, the user feedback comprising a quantitative index of pain resulting from driving the implantable stimulator device according to the user specified configuration options;

building, at the programming device, a profile for the patient user based on the user specified configuration options and the user feedback from the patient user, the profile correlates the user specified configuration options with a corresponding quantitative index of pain;

recommending, at the programming device, at least one configuration option based on the profile built from the user specified configuration options and the user feedback from the patient user when the configuration options are subsequently presented to the patient user for a treatment; and wherein receiving user feedback comprises receiving information of a quantitative index of pain expressed as improvement over a baseline of pain, the improvement resulting from driving the implanted stimulator device according to the user specified configuration options.

2. The method of claim 1, wherein establishing a communicating link between a programming device and a controller device comprises: establishing a wireless communication link between the programming device and the controller device such that data encoding configuration options are transmitted over the wireless communication link from the programming device to the controller device.

3. The method of claim 1, wherein establishing a communicating link between a programming device and a controller device comprises: establishing a wired communication link between the programming device and the controller device such that data encoding configuration options are transmitted over the wired communication link from the programming device to the controller device.

4. The method of claim 1, further comprising: presenting, on the programming device, a graphic user interface over which configuration options are presented to the patient user of the implanted passive implantable stimulator device, the specification of the configuration options are received from the patient user in response to the presented configuration options, and user feedback are received from the patient user the implanted stimulator device operating according to the user specified configuration option.

5. The method of claim 1, wherein building a profile for the patient user based on the user specified configuration options and the user feedback from the patient user comprises:
assembling user specified configuration options that include all selected permutations of the stimulation waveform parameters from various treatments; and
determining a correlation between a particular permutation of the stimulation waveform parameters with a quantitative index of pain as reported by the patient user when the correlation becomes statistically significant.

6. The method of claim 5, wherein determining a correlation between a particular permutation of the stimulation waveform parameters with a quantitative index of pain as reported by the patient user further comprises:
establishing the correlation based on a time window when the treatment is rendered.

7. The method of claim 5, wherein determining a correlation between a particular permutation of the stimulation waveform parameters with a quantitative index of pain as reported by the patient user further comprises:
determining the correlation by merging permutations of the stimulation waveform parameters when the permutations of the stimulation waveform parameters are statistically similar in inducing a particular quantitative index of pain.

8. The method of claim 1, wherein recommending at least one configuration option comprises recommending a particular permutation of stimulation waveform parameters to the patient user for the treatment.

9. The method of claim 8, further comprising: selecting the particular permutation of stimulation waveform parameters as more likely than other permutations to render a desired improvement over a baseline of pain for the treatment.

10. A programming device, coupled to a controller device to control settings on an implanted stimulator device, the programming device comprising:
a processor; and
a user interface in communication with the processor, wherein the processor is configured to perform operations of:
establishing a communication link between a programming device and a controller device, the controller device configured to wirelessly and non-inductively provide power to and assert control over a passive implantable stimulator device implanted inside a patient user;
presenting, on the programming device, configuration options to the patient user of the passive implantable stimulator device, the configuration options comprising stimulation waveform parameters for driving the passive implantable stimulator;
receiving, from the patient user and on the programming device, user specified configuration options in response to the presented configuration options;
receiving a user feedback, from the patient user and on the programming device, when the user specified configuration options are transferred to the controller device which, in turn, drives the implantable stimulator device according to the user specified configuration options, the user feedback comprising a quantitative index of pain resulting from driving the implantable stimulator device according to the user specified configuration options;
building, at the programming device, a profile for the patient user based on the user specified configuration options and the user feedback from the patient user, the profile correlates the user specified configuration options with a corresponding quantitative index of pain;
recommending, at the programming device, at least one configuration option based on the profile built from the user specified configuration options and the user feedback from the patient user when the configuration options are subsequently presented to the patient user for a treatment; and
wherein receiving user feedback comprises receiving information of a quantitative index of pain expressed as improvement over a baseline of pain, the improvement resulting from driving the implanted stimulator device according to the user specified configuration options.

11. The programming device of claim 10, wherein establishing a communicating link between the programming device and the controller device comprises: establishing a wireless communication link between the programming device and the controller device such that data encoding configuration options are transmitted over the wireless communication link from the programming device to the controller device.

12. The programming device of claim 10, wherein establishing a communicating link between the programming device and the controller device comprises: establishing a wired communication link between the programming device and the controller device such that data encoding configuration options are transmitted over the wired communication link from the programming device to the controller device.

13. The programming device of claim 10, wherein the processor is further configured to perform the operation of: presenting, on the user interface, a touch screen interface tool over which configuration options are presented to the patient user of the implanted passive implantable stimulator device, the specification of the configuration options are received from the patient user in response to the presented configuration options, and user feedback are received from the patient user the implanted stimulator device operating according to the user specified configuration option.

14. The programming device of claim 10, wherein building a profile for the patient user based on the user specified configuration options and the user feedback from the patient user comprises:

assembling user specified configuration options that include all selected permutations of the stimulation waveform parameters from various treatments; and determining a correlation between a particular permutation of the stimulation waveform parameters with a quantitative index of pain as reported by the patient user when the correlation becomes statistically significant.

15. The programming device of claim 14, wherein determining a correlation between a particular permutation of the stimulation waveform parameters with a quantitative index of pain as reported by the patient user further comprises:

establishing the correlation based on a time window when the treatment is rendered.

16. The programming device of claim 14, wherein determining a correlation between a particular permutation of the stimulation waveform parameters with a quantitative index of pain as reported by the patient user further comprises:

determining the correlation by merging permutations of the stimulation waveform parameters when the permutations of the stimulation waveform parameters are statistically similar in inducing a particular quantitative index of pain.

17. The programming device of claim 10, wherein recommending at least one configuration option comprises recommending a particular permutation of stimulation waveform parameters to the patient user for the treatment.

18. The programming device of claim 17, wherein the processor is further configured to perform an operation of: selecting the particular permutation of stimulation waveform parameters as more likely than other permutations to render a desired improvement over a baseline of pain for the treatment.

\* \* \* \* \*